US007892844B2

(12) United States Patent
Hess et al.

(10) Patent No.: US 7,892,844 B2
(45) Date of Patent: *Feb. 22, 2011

(54) DIFFERENTIATION OF CARDIAC AND PULMONARY CAUSES OF ACUTE SHORTNESS OF BREATH

(75) Inventors: Georg Hess, Mainz (DE); Andrea Horsch, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 335 days.

This patent is subject to a terminal disclaimer.

(21) Appl. No.: 11/780,560

(22) Filed: Jul. 20, 2007

(65) Prior Publication Data

US 2008/0070315 A1 Mar. 20, 2008

(30) Foreign Application Priority Data

Jul. 28, 2006 (EP) .................................. 06118090

(51) Int. Cl.
*G01N 33/49* (2006.01)
*G01N 33/00* (2006.01)

(52) U.S. Cl. ........................................ 436/86; 435/7.93
(58) Field of Classification Search .................... 436/86
See application file for complete search history.

(56) References Cited

U.S. PATENT DOCUMENTS

| 5,744,305 | A | 4/1998 | Fodor et al. | |
|---|---|---|---|---|
| 2004/0121343 | A1* | 6/2004 | Buechler et al. | 435/6 |
| 2004/0176914 | A1* | 9/2004 | Buechler et al. | 702/19 |
| 2006/0019315 | A1* | 1/2006 | Hess et al. | 435/7.1 |
| 2006/0166276 | A1* | 7/2006 | Doyle et al. | 435/7.1 |
| 2007/0037208 | A1* | 2/2007 | Foote et al. | 435/7.1 |
| 2008/0008696 | A1* | 1/2008 | Hochstrasser et al. | 424/94.5 |
| 2010/0047835 | A1* | 2/2010 | Bergmann et al. | 435/15 |
| 2010/0055683 | A1* | 3/2010 | Snider et al. | 435/6 |

FOREIGN PATENT DOCUMENTS

| EP | 0648228 B1 | 11/1998 |
|---|---|---|
| WO | 99/13337 | 3/1999 |
| WO | 02/083913 A1 | 10/2002 |
| WO | 02/089657 A2 | 11/2002 |
| WO | 2004/077056 A1 | 9/2004 |

OTHER PUBLICATIONS

Lainchbury, J. G. et al. "Brain Natriuretic Peptide and N-Terminal Brain Natriuretic Peptide in the Diagnosis of Heart Failure in Patients With Acute Shortness of Breath," Journal of the American College of Cardiology, 2003, 42, 728-735.*
Pascual Figal, D. A. et al. "Usefulness of NTproBNP in the Emergency Management of Patients With Severe Dyspnea and an Uncertain Heart Failure Diagnosis," Rev. Esp. Cardiol. 2005, 58, 1155-1161.*
Mueller, C. et al. "Use of B-Type Natriuretic Peptide in the Evaluation and Management of Acute Dyspnea," New England Journal of Medicine 2004, 350, 647-654.*
Wright, S. P. et al. "Plasma Amino-Terminal Pro-Brain Natriuretic Peptide and Accuracy of Heart-Failure Diagnosis in Primary Care," Journal of the American College of Cardiology, 2003, 42, 1794-1800.*
Baggish, A. et al., "A validated clinical and biochemical score for the diagnosis of acute heart failure: The ProBNP Investigation of Dyspnea in the Emergency Department (PRIDE) Acute Heart Failure Score," American Heart Journal, 151:1, Jan. 2006, 48-54.
Bonow, R. et al., "New Insights Into the Cardiac Natriuretic Peptides," Circulation, 93:1, Jun. 1, 1996, 1946-1950.
De Pasquale, C. et al., "Plasma Surfactant Protein-B A Novel Biomarker in Chronic Heart Failure," Circulation, Aug. 31, 2004, 1091-1096.
Doyle, I. et al., "Surfactant Proteins-A and -B Are Elevated in Plasma of Patients with Acute Respiratory Failure," Am J Respir Crit Care Med, vol. 156, 1997, 1217-1229.
Guttentag, S. et al., "Surfactant Protein B Processing in Human Fetal Lung,"The American Physiological Society, 275:3, 1998, L559-L566.
Hawgood, S., "Pulmonary surfactant apoproteins: a review of protein and genomic structure," The American Physiological Society, 257:2, 1989, L13-L22.
Karl, J. et al., "Development of a novel, N-Terminal-proBNP (NT-proBNP) assay with low detection limit," Scand J Cline Invest, 59(Suppl 230), 1999, 177-181.
Kruntz, J. et al., "NMR Structure of Lung Surfactant Peptide SP-B11-25," Biochemistry 2002, 41, 9627-9636.
Mueller, T. et al., "Long-term stability of endogenous B-type natriuretic peptides (BNP) and amino terminal pro-BNP (NT-proBNP) in frozen plasma samples," Clin Chem Lab Med, 42:8, 2004, 942-944.
Nielsen, L. et al., "N-terminal pro-brain natriuretic peptide for discriminating between cardiac and non-cardiac dyspnoea," The European Journal of Heart Failure, 6, 2004, 63-70.

(Continued)

*Primary Examiner*—Yelena G Gakh
*Assistant Examiner*—Michelle M Adams

(57) ABSTRACT

The present invention relates to a method for differentiating in a subject suffering from acute shortness of breath (dyspnea) between (i) a pulmonary disease, (ii) a cardiovascular complication, (iii) a cardiovascular complication accompanied by a pulmonary disease or (iv) acute dyspnea without cardiovascular or pulmonary causes comprising the steps of determining the amount of pulmonary surfactant protein B (SP-B) in a sample of a subject, determining the amount of N-terminal pro-brain natriuretic peptide (NT-proBNP) in a sample of the subject, and differentiating between (i) a pulmonary disease, (ii) a cardiovascular complication, (iii) a cardiovascular complication accompanied by a pulmonary disease or (iv) acute dyspnea without cardiovascular or pulmonary causes by comparing the determined amounts with reference amounts.

5 Claims, 2 Drawing Sheets

OTHER PUBLICATIONS

Nitobe, J. et al., "Surfactant Protein D May be a Novel Marker for Lung Edema in Human Heart Failure," Circulation Journal, vol. 66, Suppl I, 2002, 604.

Nolan, J. et al., "Suspension array technology: evolution of the flat-array paradigm," Trends in Biotechnology, 20:1, Jan. 2002, 9-12.

Okuyama. M. et al., "Surfactant Protein D as Host Defence Molecule in Congestive Heart Failure; Significance of Left Ventricular Dysfunction," Japanese Circulation Journal, 65; Suppl 1, 2001, p. 30.

Ray, P. et al., "Usefulness of B-type natriuretic peptide in elderly patients with acute dyspnea," Intensive Care Med, 30:2004, 2230-2236.

Smith, M. et al., "Delayed metabolism of human brain natriuretic peptide reflects resistance to neutral endopeptidase," Journal of Endocrinology, 167, 2000, 239-246.

Takahashi, H. et al., "Pulmonary Surfactant Proteins A and D: Innate Immune Functions and Biomarkers for Lung Disease," Current Pharmaceutical Design, 12, 2006, 589-598.

Wu, A. et al., "Analytical and Clinical Evaluation of the Bayer ADVIA Centaur Automated B-Type Natriuretic Peptide Assay in Patients with Heart Failure: A Multisite Study," Clinical Chemistry, 50:5, 2004, 867-873.

Yeo, K. et al., "Multicenter evaluation of the Roche NT-proBNP assay and comparison to the Biosite Triage BNP assay," Clinica Chimica Acta 338 (2003) 107-115.

Morrison, L. et lal., "Utility of a Rapid B-Natriuretic Peptide Assay in Differentiating Congestive Heart Failure from Lung Disease in Patients Present with Dyspnea," Journal of American College of Cardiology, 39;2 (2002) 202-209.

* cited by examiner ary complication accompanied by a pulmonary disease or (iv) acute dyspnea without cardiovascular or pulmonary causes comprising the steps of determining the amount of pulmonary surfactant protein (SP-B) in a sample of a subject, determining the amount of a natriuretic peptide in a sample of said subject, and differentiating between (i) a pulmonary disease, (ii) a cardiovascular complication, (iii) a cardiovascular complication accompanied by a pulmonary disease or (iv) acute dyspnea without cardiovascular or pulmonary causes by comparing the determined amounts with reference amounts. Moreover, the present invention relates to a device and a kit for carrying out said method.

US 7,892,844 B2

DIFFERENTIATION OF CARDIAC AND PULMONARY CAUSES OF ACUTE SHORTNESS OF BREATH

RELATED APPLICATIONS

This application claims priority to EP 06118090.7 filed Jul. 28, 2006.

FIELD OF THE INVENTION

The present invention relates to methods, devices and kits for differentially diagnosing the cause of acute shortness of breath. Specifically, the present invention relates to a method for differentiating in a subject suffering from acute shortness of breath (dyspnea) between (i) a pulmonary disease, (ii) a cardiovascular complication, (iii) a cardiovascular complication accompanied by a pulmonary disease or (iv) dyspnea without cardiovascular or pulmonary causes comprising the steps of determining the amount of pulmonary surfactant protein (SP-B) in a sample of a subject, determining the amount of a natriuretic peptide in a sample of said subject, and differentiating between (i) a pulmonary disease, (ii) a cardiovascular complication, (iii) a cardiovascular complication accompanied by a pulmonary disease or (iv) acute dyspnea without cardiovascular or pulmonary causes by comparing the determined amounts with reference amounts. Moreover, the present invention relates to a device and a kit for carrying out said method.

BACKGROUND

Cardiovascular complications and, in particular, acute cardiovascular events are most often life threatened medical conditions which require immediate action. However, these conditions can not always be unambiguously diagnosed. Specifically, some of the most common symptoms accompanying various types of heart diseases including acute cardiovascular events but also chronic heart dysfunctions such as chronic heart failure are symptoms which are characteristic for other (non-cardiovascular) diseases as well. Therefore, it is often difficult, cumbersome and time consuming to differentiate between a cardiovascular or other cause of an observed symptom. Said differentiation may also require the help of a specialist such as a cardiologist.

A typical symptom for cardiovascular complications, in particular, for an acute cardiovascular event or a more severe chronic heart failure is shortness of breath (dyspnea). As for other symptoms, dyspnea may have various causes including cardiovascular complications and non-cardiovascular pulmonary diseases.

In light of a potential cardiovascular cause of the symptom, it is highly advisable to properly diagnose its cause in a given patient, e.g., an emergency patient.

WO99/13337 discloses that surfactant proteins may be used as a biomarker for several specific pulmonary diseases including acute respiratory distress syndrome (ARDS).

In WO2004/077056 it is disclosed that systemic levels of surfactant proteins may be used as markers for heart failure. However, the disclosed techniques do not allow for a differential diagnosis of the cause of the elevated levels of the surfactant proteins. Specifically, it is known that pulmonary diseases or damages may also result in increased systemic levels of said proteins (Doyle 1997, Am J Respir Crit Care Med Vol. 156: 1217-1229). Accordingly, the disclosed methods shall inevitably produce false positive diagnostic results which in turn result in an inappropriate therapy (Svendstrup Nielsen, 2004, The European Journal of Heart Failure 6: 63-70).

Moreover, surfactant proteins have been described together with the N-terminal brain natriuretic peptide (NT-proBNP) to be indicative for the severity of heart failure according to the New York Heart Association (NYHA) classification (DePhasquale, 2004, Circulation 110:1091-1096).

NT-proBNP has been also described together with seven additional parameters as an indicator for acute heart failure in patients exhibiting dyspnea (Baggish 2005, American Heart Journal, 151:48-54).

SUMMARY OF THE INVENTION

Therefore, there is a clear long-standing need for means and methods allowing a differential diagnosis of the cause of symptoms such as dyspnea and, in particular, acute dyspnea, in a subject. The said means and methods shall allow a reliable efficient diagnosis and shall avoid the drawbacks of the current techniques.

Thus, the technical problem underlying the present invention must be seen as the provision of means and methods for complying with the aforementioned needs.

The technical problem is solved by the embodiments characterized in the claims and herein below.

Accordingly, the present invention relates to a method for differentiating in a subject suffering from acute shortness of breath (dyspnea) between (i) a pulmonary disease, (ii) a cardiovascular complication, (iii) a cardiovascular complication, (iii) a cardiovascular complication accompanied by a pulmonary disease or (iv) acute dyspnea without cardiovascular or pulmonary causes comprising the steps of:

a) determining the amount of a pulmonary surfactant protein which is SP-B in a sample of a subject;
b) determining the amount of a natriuretic peptide in a sample of said subject; and
c) differentiating between (i) a pulmonary disease, (ii) a cardiovascular complication, (iii) a cardiovascular complication accompanied by a pulmonary disease or (iv) acute dyspnea without cardiovascular or pulmonary causes by comparing the amounts determined in a) and b) with reference amounts.

The method of the present invention is, preferably, an in vitro method. Moreover, the method may comprise steps in addition to those explicitly referred to above such as further sample pre-treatment steps or evaluation steps.

DETAILED DESCRIPTION OF THE INVENTION

Figure 1:
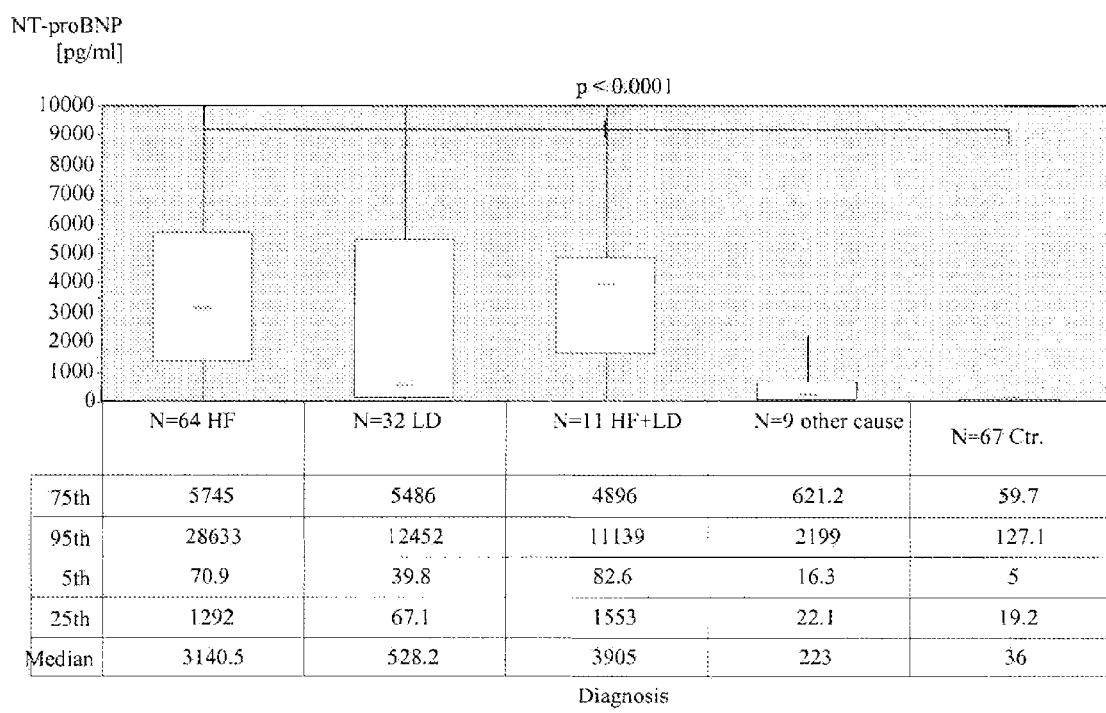
FIG. 1 shows box plots for the NT-proBNP concentration measured for a patient cohort having either heart failure (HF), a pulmonary disease (LD) or both (Comb. HF+LD) as well as the concentration in a control cohort (Ctr.). N represents the number of patients. Moreover, indicated are the median and the 75th, 95th, 5th and 25th percentiles.

The term "differentiating" as used herein means to distinguish between a subject which suffers from (i) a pulmonary disease, (ii) a cardiovascular complication, (iii) a cardiovascular complication accompanied by a pulmonary disease or (iv) acute dyspnea without cardiovascular or pulmonary causes under conditions where the subjects suffering from said disease show essentially the same symptoms, i.e. acute shortness of breath. The term as used herein, preferably, includes differentially diagnosing a pulmonary disease, a cardiovascular complication showing pulmonary symptoms, a cardiovascular complication accompanied by a pulmonary disease or acute dyspnea without cardiovascular or pulmonary causes.

Diagnosing as used herein refers to assessing the probability according to which a subject suffers from the diseases referred to in this specification. As will be understood by those skilled in the art, such an assessment is usually not intended to be correct for 100% of the subjects to be diagnosed. The term, however, requires that a statistically significant portion of subjects can be diagnosed to suffer from the said disease (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc., Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

Diagnosing according to the present invention also includes monitoring, confirmation, subclassification and prediction of the relevant disease, symptoms or risks therefor. Monitoring relates to keeping track of an already diagnosed disease, or complication, e.g. to analyze the progression of the disease or the influence of a particular treatment on the progression of disease or complication. Confirmation relates to the strengthening or substantiating a diagnosis already performed using other indicators or markers. Subclassification relates to further defining a diagnosis according to different subclasses of the diagnosed disease, e.g. defining according to mild and severe forms of the disease. Prediction relates to prognosing a disease or complication before other symptoms or markers have become evident or have become significantly altered.

The expression "acute shortness of breath" or "acute dyspnea" refers to an impaired respiration which results in an increase respiratory frequency and/or an increased respiratory volume. Thus, shortness of breath may result, preferably, in hyperventilation. Shortness of breath occurs, usually, at an oxygen saturation level below the normal oxygen saturation level of at least 95%. Acute dyspnea as used herein refers to a non-permanently occurring shortness of breath, i.e. shortness of breath which occurs all over sudden (acute onset dyspnea) and which is not correlated to a specific condition, e.g., which occurs only under certain types of stress etc. Moreover, acute dyspnea persists no longer than 2 weeks from the acute onset, while chronic dyspnea is characterized as persisting for a period of time longer than 2 weeks. Furthermore, acute dyspnea is, usually, progressively worsening.

The term "pulmonary disease" refers to any disease which causes shortness of breath. Moreover, it is envisaged that a pulmonary disease as referred to in accordance with the present invention shall result in an impaired alveolocapillary membrane barrier having an increased permeability for surfactant proteins, in particular for the pulmonary surfactant protein specifically referred to herein. Said disease is, preferably, acute and chronic respiratory failure, pulmonary fibrosis, pulmonary proteinosis, pulmonary edema, pulmonary inflammation, pulmonary emphysema obesity, thyroid diseases or, more preferably, a pulmonary embolism.

The term "cardiovascular complication" as used herein refers to any acute or chronic disorder of the cardiovascular system. Acute disorders of the cardiovascular system include acute cardiovascular events. Thus, more preferably, encompassed are stable angina pectoris (SAP) or acute coronary syndromes (ACS). ACS patients can show unstable angina pectoris (UAP) or these individuals have already suffered from a myocardial infarction (MI). MI can be an ST-elevated MI or a non-ST-elevated MI. The occurring of an MI can be followed by a left ventricular dysfunction (LVD). Also encompassed by the term are chronic disorders and, preferably, heart failure. It is to be understood that the term also includes medical conditions and diseases which cause heart failure in addition to the aforementioned acute cardiovascular events, such as congenital or acquired heart valve diseases or disorders, myocarditis, myocardiopathy, amyloidosis or hemochromatosis. Further preferred cardiovascular diseases are thrombosis, preferably arterial thrombosis, or diseases causing blood vessel calcification, preferably atherosclerosis, as well as stroke.

The individuals suffering from a cardiovascular complication may show clinical symptoms (e.g. dyspnea, chest pain, see also NYHA classification below). Specifically, symptoms of cardiovascular diseases have been classified into a functional classification system according to the New York Heart Association (NYHA). Patients of Class I have no obvious symptoms of cardiovascular disease. Physical activity is not limited, and ordinary physical activity does not cause undue fatigue, palpitation, or dyspnea. Patients of class II have slight limitation of physical activity. They are comfortable at rest, but ordinary physical activity results in fatigue, palpitation, or dyspnea. Patients of class III show a marked limitation of physical activity. They are comfortable at rest, but less than ordinary activity causes fatigue, palpitation, or dyspnea. Patients of class IV are unable to carry out any physical activity without discomfort. They show symptoms of cardiac insufficiency at rest. If any physical activity is undertaken, discomfort is increased. Another characteristic of cardiovascular complication can be the "left ventricular ejection fraction" (LVEF) which is also known as "ejection fraction". People with a healthy heart usually have an unimpaired LVEF, which is generally described as above 50%. Most people with a systolic heart disease which is symptomatic generally have an LVEF of 40% or less.

Preferably, a subject suffering from a cardiovascular complication and exhibiting acute dyspnea in accordance with the present invention can be allocated to an intermediated NYHA class, preferably, to NYHA class I, II or III and, most preferably, to NYHA class II.

By "a cardiovascular complication accompanied by a pulmonary disease" it is meant that the subject shall suffer from a cardiovascular complication and from a pulmonary disease. It is to be understood that the two diseases or disorders may appear independently, i.e. without one causing the other. However, cases in which a primary cardiovascular complication as referred to herein causes a secondary pulmonary diseases and vice versa are also, preferably, encompassed from the above expression.

Further, acute dyspnea may, whatsoever, be observed in patients which neither suffer from cardiovascular complications nor from pulmonary diseases. Such cases shall be comprised by the term "acute dyspnea without cardiovascular or pulmonary causes" for the purpose of the present invention. Preferred non-cardiovascular and non-pulmonary causes of acute shortness of breath are, preferably, obesity, high body weight, an untrained or poorly trained physical condition of the subject, psychological conditions such as anxiety states.

The term "subject" as used herein relates to animals, preferably mammals, and, more preferably, humans. However, it is envisaged by the present invention that the subject shall, preferably, exhibit acute shortness of breath.

Determining the amount of a natriuretic peptide or pulmonary surfactant protein according to the present invention relates to measuring the amount or concentration, preferably semi-quantitatively or quantitatively. Measuring can be done directly or indirectly. Direct measuring relates to measuring the amount or concentration of the natriuretic peptide or the pulmonary surfactant protein based on a signal which is obtained from the natriuretic peptide or the pulmonary surfactant protein itself and the intensity of which directly correlates with the number of molecules of the peptide present in the sample. Such a signal—sometimes referred to herein as intensity signal—may be obtained, e.g., by measuring an intensity value of a specific physical or chemical property of the natriuretic peptide or the pulmonary surfactant protein. Indirect measuring includes measuring of a signal obtained from a secondary component (i.e. a component not being the natriuretic peptide itself) or a biological read out system, e.g., measurable cellular responses, ligands, labels, or enzymatic reaction products.

In accordance with the present invention, determining the amount of the natriuretic peptide or the pulmonary surfactant protein can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the natriuretic peptide of the pulmonary surfactant protein. Moreover, the signal strength can, preferably, be correlated directly or indirectly (e.g. reverse-proportional) to the amount of polypeptide present in a sample. Further suitable methods comprise measuring a physical or chemical property specific for the natriuretic peptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on Elecsys analyzers), CBA (an enzymatic cobalt binding assay, available for example on Roche-Hitachi analyzers), and latex agglutination assays (available for example on Roche-Hitachi analyzers).

Preferably, the method for determining the amount of a natriuretic peptide or pulmonary surfactant protein comprises the steps of (a) contacting a cell capable of eliciting a cellular response the intensity of which is indicative of the amount of the peptide with the peptide for an adequate period of time, (b) measuring the cellular response.

For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide.

Also preferably, the method for determining the amount of a natriuretic peptide or a pulmonary surfactant protein comprises the step of measuring a specific intensity signal obtainable from the natriuretic peptide or a pulmonary surfactant protein in the sample.

As described above, such a signal may be the signal intensity observed at an m/z variable specific for the natriuretic peptide or a pulmonary surfactant protein observed in mass spectra or a NMR spectrum specific for the natriuretic peptide or a pulmonary surfactant protein.

The method for determining the amount of a natriuretic peptide may also preferably comprise the steps of (a) contacting the peptide with a specific ligand, (b) (optionally) removing non-bound ligand, (c) measuring the amount of bound ligand.

The bound ligand will generate an intensity signal. Binding according to the present invention includes both covalent and non-covalent binding. A ligand according to the present invention can be any compound, e.g., a peptide, polypeptide, nucleic acid, or small molecule, binding to the natriuretic peptide or the pulmonary surfactant protein described herein. Preferred ligands include antibodies, nucleic acids, peptides or polypeptides such as receptors for the natriuretic peptides or binding partners for the pulmonary surfactant protein and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)2 fragments that are capable of binding antigen or hapten. The present invention also includes humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the natriuretic peptide. Specific binding according to the present invention means that the ligand or agent should not bind substantially to ("cross-react" with) another peptide, polypeptide or substance present in the sample to be analyzed. Preferably, the specifically bound natriuretic peptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g. by NMR, mass spectrometry or surface plasmon resonance.

Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the ligand/natriuretic peptide or ligand/pulmonary surfactant protein complex or the ligand which was bound by the natriuretic peptide or the pulmonary surfactant protein, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for an detectable, preferably measurable, amount of product to be produced. Instead of measuring the amount of product, the time necessary for appearance of a given (e.g. detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxigenin, His-tag, glutathione-S-transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB). 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemiluminescence, which can be measured according to methods known in the art (e.g. using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include $^{35}S$, $^{125}I$, $^{32}P$, $^{33}P$ and the like. A radioactive label can be detected by any method known and appropriate, e.g. a light-sensitive film or a phosphor imager. Suitable measurement methods according the present invention also include precipitation (particularly immunoprecipitation), electro-chemiluminescence (electro-generated chemiluminescence), RIA (radioimmunoassay), ELISA (enzyme-linked immunosorbent assay), sandwich enzyme immune tests, electro-chemiluminescence sandwich immunoassays (ECLIA), dissociation-enhanced lanthanide fluoroimmunoassay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamide gel electrophoresis (SDS-PAGE), Western Blotting, and mass spectrometry), can be used alone or in combination with labeling or other detection methods as described above.

Furthermore, the method for determining the amount of a natriuretic peptide, preferably, comprises (a) contacting a solid support comprising a ligand for the natriuretic peptide or the pulmonary surfactant protein as specified above with a sample comprising the natriuretic peptide or the pulmonary surfactant protein and (b) measuring the amount of the natriuretic peptide or the pulmonary surfactant protein which is bound to the support.

The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan J P, Sklar L. A. (2002). Suspension array technology: evolution of the flat-array paradigm. Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744, 305).

The term "amount" as used herein encompasses the absolute amount of the natriuretic peptides or the pulmonary surfactant protein, the relative amount or concentration of the natriuretic peptides or the pulmonary surfactant protein as well as any value or parameter which correlates thereto. Such values or parameters comprise intensity signal values from all specific physical or chemical properties obtained from the natriuretic peptides or the pulmonary surfactant protein by direct measurements, e.g., intensity values in mass spectra or NMR spectra. Moreover, encompassed are all values or parameters which are obtained by indirect measurements specified elsewhere in this description, e.g., expression levels determined from biological read out systems in response to the natriuretic peptide or the pulmonary surfactant protein or intensity signals obtained from specifically bound ligands. It is to be understood that values correlating to the aforementioned amounts or parameters can also be obtained by all standard mathematical operations.

The term "pulmonary surfactant protein" as used in this specification relates to pulmonary surfactant protein B (SP-B). The term, preferably, refers to the human proteins as well as variants thereof, preferably, allelic variants or species specific homologs, paralogs, or orthologs. The human proteins are well characterized in the prior art and disclosed, e.g., in Hawgood, 1989, Am J Physiol—Lung Cellular and Molecular Physiology, Vol 257, Issue 2:13-L22 (for all surfactant proteins), Takahashi 2006, Curr Pharm Des, 12(5):589-598 (for SP-A and SP-D), and Kurutz 2002, Biochemistry, 41(30):9627-9636, Guttentag 1998, Am J Physiol—Lung Cellular and Molecular Physiology, Vol 275, Issue 3:L559-L566 (for SP-B).

Specifically, envisaged are also variants of pulmonary surfactant proteins which are on the amino acid level at least 60% identical, more preferably at least 70%, at least 80%, at least 90%, at least 98% or at least 99% identical, to the human pulmonary surfactant proteins. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of a human pulmonary surfactant protein as long as the said polypeptides have pulmonary surfactant protein properties, pulmonary surfactant protein properties as referred to herein are immunological and/or biological properties. Preferably, the pulmonary surfactant protein variants have immunological properties (i.e. epitope composition) comparable to those of the pulmonary surfactant proteins specifically referred to herein. Thus, the variants shall be recognizable by the aforementioned means or ligands used for determination of the pulmonary surfactant protein. Variants also include posttranslationally modified pulmonary surfactant proteins such as glycosylated proteins.

Moreover, it is to be understood that the term also encompasses any combination of the aforementioned specific pulmonary surfactant proteins or variants thereof. For example, SP-B may be determined in combination with SP-D or SP-A or both.

The term "natriuretic peptide" comprises Atrial Natriuretic Peptide (ANP)-type and Brain Natiuretic Peptide (BNP)-type peptides and variants thereof having the same predictive potential. Natriuretic peptides according to the present invention comprise ANP-type and BNP-type peptides and variants thereof (see e.g. Bonow, R. O. (1996). New insights into the cardiac natriuretic peptides. Circulation 93:1946-1950).

ANP-type peptides comprise pre-proANP, proANP, NT-proANP, and ANP.

BNP-type peptides comprise pre-proBNP, proBNP, NT-proBNP, and BNP.

The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP).

Preferred natriuretic peptides according to the present invention are NT-proANP, ANP, NT-proBNP, BNP, and variants thereof. ANP and BNP are the active hormones and have a shorter half-life than their respective inactive counterparts, NT-proANP and NT-proBNP, BNP is metabolized in the blood, whereas NT-proBNP circulates in the blood as an intact molecule and as such is eliminated renally. The in-vivo half-life of NT-proBNP is 120 min longer than that of BNP, which is 20 min (Smith M W, Espiner E A, Yandle T G, Charles C J, Richards A M. Delayed metabolism of human brain natriuretic peptide reflects resistance to neutral endopeptidase. J. Endocrinol. 2000; 167:239-46).

Preanalytics are more robust with NT-proBNP allowing easy transportation of the sample to a central laboratory (Mueller T, Gegenhuber A, Dieplinger B, Poelz W, Haltmayer M. Long-term stability of endogenous B-type natriuretic peptide (BNP) and amino terminal proBNP (NT-proBNP) in frozen plasma samples. Clin Chem Lab Med 2004; 42:942-4). Blood samples can be stored at room temperature for several days or may be mailed or shipped without recovery loss. In contrast, storage of BNP for 48 hours at room temperature or at 4° Celsius leads to a concentration loss of at least 20% (Mueller T, Gegenhuber A, et al., Clin Chem Lab Med 2004; 42:942-4, supra; Wu A H, Packer M, Smith A, Bijou R, Fink D, Mair J, Wallentin L, Johnston N, Feldcamp C S, Haverstick D M, Ahnadi C E, Grant A, Despres N, Bluestein B, Ghani F. Analytical and clinical evaluation of the Bayer ADVIA Centaur automated B-type natriuretic peptide assay in patients with heart failure: a multisite study. Clin Chem 2004; 50: 867-73). Therefore, depending on the time-course or properties of interest, either measurement of the active or the inactive forms of the natriuretic peptide can be advantageous.

The most preferred natriuretic peptides according to the present invention are NT-proBNP or variants thereof. As briefly discussed above, the human NT-proBNP as referred to in accordance with the present invention is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913, Bonow 1996, New Insights into the cardiac natriuretic peptides. Circulation 93: 1946-1950. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein.

The NT-proBNP referred to in accordance with the present invention further encompasses allelic and other variants of said specific sequence for human NT-proBNP discussed above. Specifically, envisaged are variant polypeptides which are on the amino acid level at least 60% identical, more preferably at least 70%, at least 80%, at least 90%, at least 95%, at least 98% or at least 99% identical, to human NT-proBNP. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the said polypeptides have NT-proBNP properties. NT-proBNP properties as referred to herein are immunological and/or biological properties. Preferably, the NT-proBNP variants have immunological properties (i.e. epitope composition) comparable to those of NT-proBNP. Thus, the variants shall be specifically recognizable (i.e. without cross reactions) by the aforementioned means or ligands used for determination of the amount of the natriuretic peptides. Biological and/or immunological NT-proBNP properties can be detected by the assay described in Karl et al. (Karl 1999, Development of a novel, N-Terminal-proBNP (NT-proBNP) assay with a low detection limit. Scand J Clin Invest 230:177-181), Yeo et al. (Yeo 2003, Multicenter evaluation of the Roche NT-proBNP assay and comparison to the Biosite Triage assay. Clinica Chimica Acta 338:107-115), and in the Example, below. Variants also include posttranslationally modified natriuretic peptides such as glycosylated peptides.

A variant in accordance with the present invention is also a peptide or polypeptide, which has been modified after collection of the sample, for example by covalent or non-covalent attachment of a label, particularly a radioactive or fluorescent label, to the peptide.

Moreover, it is to be understood that the term also relates to any combination of the aforementioned specific natriuretic peptides.

The term "sample" refers to a sample of a body fluid, to a sample of separated cells or to a sample from a tissue or an organ. Samples of body fluids can be obtained by well known techniques and include, preferably, samples of blood, plasma, serum or urine. Tissue or organ samples may be obtained from any tissue or organ by, e.g., biopsy. Separated cells may be obtained from the body fluids or the tissues or organs by separating techniques such as centrifugation or cell sorting.

Comparing as used herein encompasses comparing the amount of the natriuretic peptide or the pulmonary surfactant protein comprised by the sample to be analyzed with an amount of a suitable reference source specified below in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e. automatically providing a differential diagnosis for the diseases referred to herein in a suitable output format.

The term "reference amount" as used herein refers to an amount which allows assessing whether a subject suffers from any one of the aforementioned diseases or disorders by a comparison as referred to above. Accordingly, the reference may either be derived from a subject suffering from (i) a pulmonary disease, (ii) a cardiovascular complication, (iii) a cardiovascular complication accompanied by a pulmonary disease or (iv) acute dyspnea without cardiovascular or pulmonary causes, i.e. from a healthy subject with respect to cardiovascular complications and pulmonary diseases. It is to be understood that if a reference from a subject is used which suffers from a disease or combination of diseases, an amount of a peptide or protein in a sample of a test subject being essentially identical to said reference amount shall be indicative for the respective disease or combination of diseases. If a reference from a healthy subject is used, an amount of a peptide or protein in a sample of a test subject which significantly differs from the reference (i.e. from the normal values of the surfactant proteins and natriuretic peptides referred to herein) shall indicate a disease. The reference amount applicable for an individual subject may vary depending on various physiological parameters such as age, gender, or subpopulation. Thus, a suitable reference amount may be determined by the method of the present invention from a reference sample to be analyzed together, i.e. simultaneously or subsequently, with the test sample.

It has been found in the studies underlying the present invention that in case elevated amounts for the pulmonary surfactant protein are determined but no or only weak elevated amounts of the natriuretic peptides are determined, the subject shall merely suffer from a pulmonary disease. In case the determined amounts of the natriuretic peptide and the surfactant protein are both elevated with respect to the normal ranges, the subject shall suffer from a cardiovascular complication. If the amount of the natriuretic peptide is significantly strong elevated and the amount of the surfactant protein is elevated, too, the subject shall suffer from a cardiovascular complication accompanied by a pulmonary disease. Finally, if none of the determined amounts is elevated with respect to the reference, the subject shall exhibit acute dyspnea due to non-cardiovascular, non-pulmonary causes specified elsewhere in this description. The normal physiological (i.e. not elevated) range for the amounts of SP-B, is 12,000 to 20,000 ng/ml, preferably 20,000 ng/ml. The normal physiological (i.e. not elevated range) for natriuretic peptides and in particular for NT-proBNP is 80 to 150 pg/ml, preferably 125 pg/ml. Significantly strong elevated as used herein are amounts of natriuretic peptides and, preferably, of NT-proBNP which are larger than or equal to 3,200 pg/ml. It is to be understood that the aforementioned amounts may vary due to statistics and errors of measurement.

Advantageously, it has been found that the amount of pulmonary surfactant protein in combination with the amount of NT-pro BNP present in a sample of a subject showing pulmonary symptoms, in particular, acute shortness of breath, allow for a differential diagnosis with respect to the cause of the said symptoms. Thanks to the present invention, subjects and in particular emergency patients can be more readily and reliably diagnosed and subsequently treated according to the result of the said differential diagnosis.

The explanations and definitions of the terms made above and herein below apply accordingly for all embodiments characterized in this specification and the claims.

The following embodiments are particularly preferred embodiments of the method of the present invention.

In a preferred embodiment of the method of the present invention, the pulmonary disease of the cardiovascular complication accompanied by a pulmonary disease (see (iii), above) is caused by the cardiovascular complication.

In a preferred embodiment of the method of the present invention, the cardiovascular complication of (iii) is caused by the pulmonary disease.

In another preferred embodiment of the method of the present invention, the pulmonary disease of (iii) is independent on the cardiovascular complication.

In a furthermore preferred embodiment of the method of the present invention, a reference amount less than 125 pg/ml for the natriuretic peptide and a reference amount larger than 20,000 ng/ml for SP-B are indicative for (i) a pulmonary disease.

In a furthermore preferred embodiment of the method of the present invention, a reference amount larger than 125 pg/ml but less than 3,200 pg/ml for the natriuretic peptide and a reference amount less than 20,000 ng/ml for SP-B are indicative for (ii) a cardiovascular complication.

In a further preferred embodiment of the method of the present invention, a reference amount of larger than 3,200 pg/ml for the natriuretic peptide and a reference amount lager than 20,000 ng/ml for SP-B are indicative for (iii) a pulmonary disease accompanied by a cardiovascular complication.

In another preferred embodiment of the method of the present invention, a reference amount less than 125 pg/ml for the natriuretic peptide and a reference amount less than 20,000 ng/ml for SP-B are indicative for (iv) acute chronic dyspnea without cardiovascular or pulmonary causes.

Also, in a preferred embodiment of the method of the present invention, said sample is blood, plasma, serum or urine.

In another preferred embodiment of the method of the present invention, said natriuretic peptide is NT-proBNP.

Moreover, in a preferred embodiment of the method of the present invention, said subject is a human.

Furthermore, the present invention relates to a device for differentiating between (i) a pulmonary disease, (ii) a cardiovascular complication showing pulmonary symptoms, (iii) a cardiovascular complication accompanied by a pulmonary disease or (iv) acute dyspnea without cardiovascular or pulmonary causes in a subject exhibiting acute dyspnea comprising a) means for determining the concentration of a pulmonary surfactant protein which is SP-B in a sample of a subject;
b) means for determining the amount of a natriuretic peptide or a variant thereof in a sample of a subject; and
c) means for comparing the amounts determined with a suitable reference, whereby it is differentiated between (i) a pulmonary disease, (ii) a cardiovascular complication, (iii) a cardiovascular complication accompanied by a pulmonary disease or (iv) acute dyspnea without cardiovascular or pulmonary causes.

The term "device" as used herein relates to a system of means comprising at least the aforementioned means operatively linked to each other as to allow the prediction. Preferred means for determining the amount of the natriuretic peptides or the pulmonary surfactant protein and means for carrying out the comparison are disclosed above in connection with the method of the invention. How to link the means in an operating manner will depend on the type of means included into the device. For example, where means for automatically determining the amount of the peptides are applied, the data obtained by said automatically operating means can be processed by, e.g., a computer program in order to diagnose or distinguish between the diseases referred to herein. Preferably, the means are comprised by a single device in such a case. Said device may accordingly include an analyzing unit for the measurement of the amount of the peptides in a sample and a computer unit for processing the resulting data for the differential diagnosis. Alternatively, where means such as test stripes are used for determining the amount of the peptides, the means for diagnosing may comprise control stripes or tables allocating the determined amount to an amount known to be accompanied with (i) a pulmonary disease, (ii) a cardiovascular complication, (iii) a cardiovascular complication accompanied by a pulmonary disease or (iv) acute dyspnea without cardiovascular or pulmonary causes or a healthy control subject. The test stripes are, preferably, coupled to a ligand which specifically binds to the natriuretic peptide or pulmonary surfactant protein. The strip or device, preferably, comprises means for detection of the binding of said peptides to the said ligand. Preferred means for detection are disclosed in connection with embodiments relating to the method of the invention above. In such a case, the means are operatively linked in that the user of the system brings together the result of the determination of the amount and the diagnostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test stripes or electronic devices which merely require loading with a sample. The results may be given as output of diagnostic raw data which need interpretation by the medical practitioner. Preferably, the output of the device are, however, processed diagnostic raw data the interpretation of which does not require a specialized medical practitioner. Further preferred devices comprise the analyzing units/devices (e.g., biosensors, arrays, solid supports coupled to ligands specifically recognizing the natriuretic peptide, plasmon surface resonance devices, NMR spectrometers, mass-spectrometers etc.) or evaluation units/devices referred to above in accordance with the method of the invention.

Finally, the present invention relates to a kit for carrying out the methods of the present invention, wherein said kit comprises a) means for determining the concentration of a pulmonary surfactant protein which is SP-B in a sample of a subject;
b) means for determining the amount of a natriuretic peptide or a variant thereof in a sample of a subject; and
c) means for comparing the amounts determined with a suitable reference, whereby (i) a pulmonary disease, (ii) a cardiovascular complication, (iii) a cardiovascular complication accompanied by a pulmonary disease or (iv) acute dyspnea without cardiovascular or pulmonary causes can be differentiated from each other.

The term "kit" as used herein refers to a collection of the aforementioned means, preferably, provided in separately or within a single container. The container, also preferably, comprises instructions for carrying out the method of the present invention.

All references cited in this specification are herewith incorporated by reference with respect to their entire disclosure content and the disclosure content specifically mentioned in this specification.

Specific Embodiments

The following example merely illustrates the invention. It shall, whatsoever, not be construed as to limit the scope of the invention.

Example

Prospective Study on Patients with Acute Dyspnea

A cohort of 214 patients suffering from acute dyspnea has been clinically investigated for the presence of heart failure, pulmonary disease or combination of both diseases. The allocation of the patients into the three disease groups has been confirmed by clinical examination, ECG and echocardiography. Blood samples of the patients have been analyzed by the prototype SP-B ELISA (Flinders assay protocol for the SP-B amounts and by the Elecsys NT-proBNP assay (Roche Diagnostics) for NT-proBNP concentrations.

The result of the determination of the NT-proBNP concentration is shown in FIG. 1. Patients suffering from a combination of both diseases (heart failure and pulmonary disease) show strongly elevated NT-proBNP levels, patients suffering from heart failure show elevated NT-proBNP levels. However, patients suffering from pulmonary disease only show weak elevated or normal NT-proBNP levels.

Figure 2:
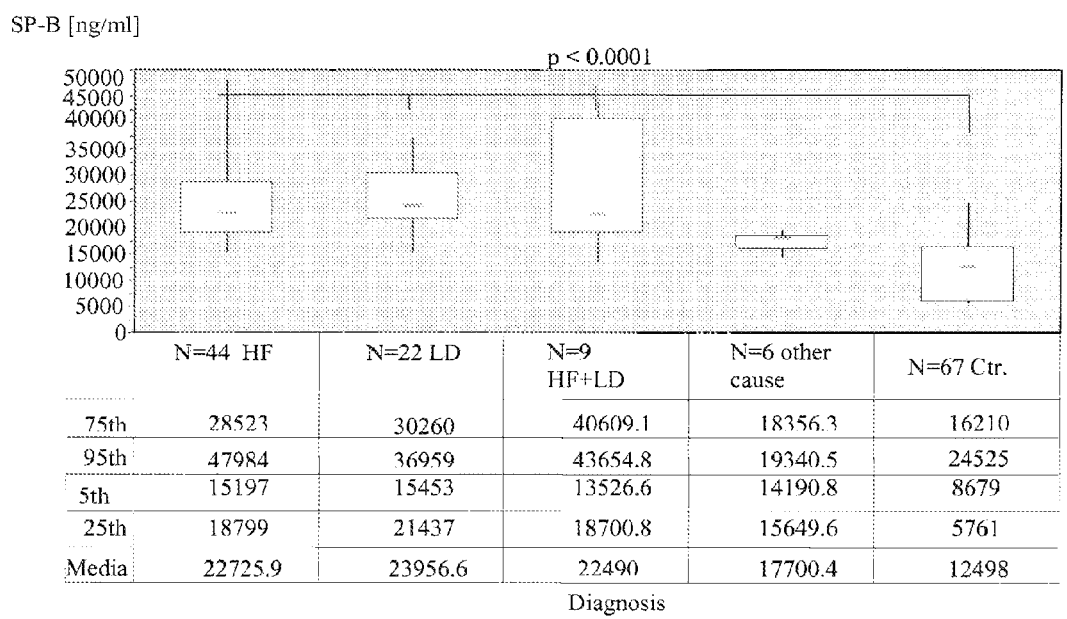
FIG. 2 shows box plots for the SP-B concentration measured for a patient cohort having either heart failure (HF), a pulmonary disease (LD) or both (Comb. HF+LD) as well as the concentration in a control cohort (Ctr.). N represents the number of patients. Moreover, indicated are the median and the 75th, 95th, $5^{th}$, and 25th percentiles.

FIG. 2 shows the outcome of the determination of the SP-B amount in the different patient groups. Pulmonary diseases or a combination of both diseases show elevated amounts of SP-B. Patients exhibiting acute dyspnea due to non-cardiac and/or non pulmonary causes show no significantly elevated SP-B with respect to the reference values described in the literature.

What is claimed is:

1. A method for differentiating in a human subject suffering from acute shortness of breath (dyspnea) between (i) a pulmonary disease, (ii) a cardiovascular complication, (iii) a cardiovascular complication accompanied by a pulmonary disease, and (iv) acute dyspnea without cardiovascular or pulmonary causes comprising the steps of determining an amount of pulmonary surfactant protein B (SP-B) in a sample from said subject, determining an amount of N-terminal pro-brain natriuretic peptide (NT-proBNP) in a sample from said subject, and comparing the amounts of SP-B and NT-proBNP determined with reference amounts of SP-B and NT-proBNP determined in a sample from a reference subject, wherein (i) a reference amount less than 125 pg/ml for NT-proBNP and a reference amount larger than 20,000 ng/ml for SP-B indicate diagnosis for pulmonary disease, (ii) a reference amount larger than 125 pg/ml but less than 3,200 pg/ml for NT-proBNP and a reference amount larger than 20,000 ng/ml for SP-B indicate diagnosis for cardiovascular complication, (iii) a reference amount larger than 3,200 pg/ml for NT-proBNP and a reference amount larger than 20,000 ng/ml for SP-B indicate diagnosis for pulmonary disease accompanied by a cardiovascular complication, and (iv) a reference amount less than 125 pg/ml for NT-proBNP and a reference amount less than 20,000 ng/ml for SP-B indicate diagnosis for acute dyspnea without cardiovascular or pulmonary causes.

2. The method of claim 1 wherein the pulmonary disease in (iii) is caused by the cardiovascular complication.

3. The method of claim 1 wherein the cardiovascular complication in (iii) is caused by the pulmonary disease.

4. The method of claim 1 wherein the pulmonary disease in (iii) is independent of the cardiovascular complication.

5. The method of claim 1 wherein said samples are selected from the group consisting of blood, plasma, serum, and urine.

* * * * *